United States Patent [19]

Sipos

[11] 4,160,821

[45] Jul. 10, 1979

[54] TREATMENT FOR GINGIVITIS

[75] Inventor: Tibor Sipos, Lebanon, N.J.

[73] Assignee: Johnson & Johnson, New Brunswick, N.J.

[21] Appl. No.: 881,207

[22] Filed: Feb. 27, 1978

[51] Int. Cl.² .................. A61K 7/16; A61K 7/24; A61K 31/315; A61K 33/30

[52] U.S. Cl. ........................ 424/49; 424/55; 424/145; 424/235; 424/289

[58] Field of Search .............. 424/49, 145, 235

[56] References Cited

U.S. PATENT DOCUMENTS

| | | | |
|---|---|---|---|
| 2,748,781 | 6/1956 | Collat | 424/145 |
| 4,022,880 | 5/1977 | Vinson et al. | 424/49 |

FOREIGN PATENT DOCUMENTS 1188353  4/1970  United Kingdom.

OTHER PUBLICATIONS

J. Clinical Periodontology 2, 33–43 (1975)—Compton et al.
Oral Res. Abst. 4(3) p. 262–Abst. #1754—Bittner et al.
Helvitica Odontologica Acta, vol. 18(1), pp. 22–24 (1974)—Schmid et al.
Dental and Oral Biology 54(5) Abst. #24644, pp. 2370-1972—Grafar et al.
Jour. A.D.A., 27(9) pp. 1379-1393 (1940)—Hanke.

Primary Examiner—Albert T. Meyers
Assistant Examiner—D. W. Robinson
Attorney, Agent, or Firm—I. Newman

[57] ABSTRACT

A glycerine solution of zinc chloride or another pharmaceutically acceptable zinc salt that is soluble in glycerine provides effective therapy for gingivitis when applied to the gingivae and teeth.

10 Claims, No Drawings

TREATMENT FOR GINGIVITIS

TECHNICAL FIELD

Normal gingivae are pink and firmly attached to the underlying alveolar bone. At the enamel-gingival junction, the gingiva forms an epithelial-lined ridge around the teeth. The area between the enamel and the gingivae is called the gingival crevice. Gingivitis develops when large masses of bacteria clog the gingival crevice.

Bacteria invade the surrounding area and form a sticky matrix, called plaque. If plaque is left undisturbed, it calcifies into calculus. Bacteria in plaque produce metabolic by-products, enzymes and toxins. These products diffuse into the immediate surrounding area, irritate the gingivae, and, as a consequence, they trigger a localized inflammatory reaction. The gingivae swell, become reddened and extrude crevicular fluid. Depending on the severity of the condition, the gingivae become sensitive to touch and may spontaneously bleed. As gingivitis advances to periodontitis, the supporting collagen fibers and the alveolar bone begin to degenerate. As a result, teeth become mobile and eventually fall out.

BACKGROUND ART

There are numerous studies that demonstrate that the accumulated plaque at the enamel-gingival junction significantly increases the severity of the gingival disease, while other studies show that when plaque is removed, healthy condition is reestablished. Because of the apparent direct cause and effect relationship between plaque and gingival inflammation, it is widely believed that plaque accumulation is detrimental to gingival health.

It has been suggested that if the accumulation of plaque at the enamel-gingival junction can be prevented or at least retarded, the severity of gingivitis and periodontitis can thereby be reduced.

Compton and Beagrie (Journal of Clinical Periodontology:1975:2:33–43) tested the effectiveness of a quaternary ammonium compound, benzethonium chloride, and zinc chloride in preventing plaque and gingivitis. The above two agents were tested separately and also in combination. According to the authors, the results showed no significant differences in the gingival scores after a ten day test period during which the results of using mouthwashes comprising 1 part glycerine to 20 parts of water and containing (a) 0.22% by weight $ZnCl_2$, (b) 0.075% benzethonium chloride, and (c) a combination of the two were compared to the results with the placebo treated group. Use of the mouthwash containing the benzethonium chloride alone was found to result in about 42% less plaque formation after the 10 day period than did use of the placebo, the combination, or the $ZnCl_2$ only mouthwashes. Thus the zinc chloride alone was ineffective as a plaque inhibitor, too. In the late forties, the combination of zinc chloride with potassium ferro-cyanide was tried for the prevention of tooth decay with varying results. (Positive results were reported by Gillard et al in The Journal of the Houston District Dental Society, Vol. 21, No. 3, pp. 2 and 3, March, 1949. Negative results with the same combination were reported by Ast et al in The Journal of the American Dental Association 41(4):437–442, October, 1950. No mention was made in either article of any effect of zinc chloride or the combination on gingivitis.)

Zinc chloride, in high concentrations, 8 to 40%, has been used as an astringent to achieve gingival retraction (Oral Research Abstracts Vol. 4, No. 3, p. 262 Abstract No. 1754). Loe and Silness, J. Pros. Dent. 13:318–328, March-April, 1963, described a procedure in which cotton strings were soaked in an 8% zinc chloride solution before application. The impregnated strings were forced to the bottom of the gingival pockets, by means of a thin steel instrument, and left in place for 10 minutes. Histological studies showed that the 8% zinc chloride-impregnated cotton strings necrotize the epithelial cuff and the adjacent layer of the subepithelial connective tissue.

Zinc chloride-containing antiseptic preparations have been widely used in the past. It is stated in "Accepted Dental Therapeutics" 1971/1972, 34th Edition, p. 200 that zinc chloride has antiseptic, astringent and escharotic activities. At concentrations of 1:2000 (0.05%) to 1:500, (0.2%) a zinc chloride solution has a weak antiseptic action. The authors conclude that "daily use of a mouthwash containing zinc chloride for so-called oral hygiene cannot be considered rational."

Schmid et al, in an article entitled "Effect of a Zinc Chloride Mouthrinse on Calculous Deposits Formed on Foils", Helvitica Odontologica Acta, Vol. 18(1):22–24, 1974, reported that a 0.2% zinc chloride-containing mouthrinse, when administered twice daily over a one week period, significantly inhibited the formation of calculus deposits collected from foils attached to lower incisors.

Gafar et al, Dental and Oral Biology Abstracts, Vol. 54(5)2370, No. 24644, reported that, after the mechanical removal of calculus from teeth, fluoride should be applied to teeth, and an anti-inflammatory treatment with zinc chloride should be applied to the gums.

In U.S. Pat. No. 4,022,880, issued May 10, 1977 to L. J. Vinson and L. P. Cancro, an improved composition for inhibiting dental plaque and calculus formation is disclosed, which comprises a combination of zinc ions and a non-toxic, organoleptically acceptable antibacterial agent. It is taught by the patentees at column 4, lines 1–16, that the use of a zinc compound alone, while affording some anticalculus action, would not produce the desired effect. They disclose, further, at column 4, lines 20–28, that zinc compounds alone or antibacterial agents alone provide only about one-half the protection against dental calculus development as do the compositions claimed in that patent.

Hanke, Jour. A.D.A, Vol. 27, No. 9, September, 1940, pp. 1379–1393, in Table 1, on pages 1384–5, indicates that various concentrations of zinc acetate, lactate and salicylate in 15% glycerol do not have bactericidal effectiveness. However, at page 1388, the author indicates that the use of a zinc acetate solution as a mouth rinse will cause plaque to disappear from even unbrushed teeth, although it is not effective in all cases and the solution appears to lose effectiveness on aging.

DISCLOSURE OF INVENTION

It has now been discovered that the rate of development of gingivitis, as characterized by inflammation, bleeding and swelling, can be substantially prevented or retarded by the daily application to the gingivae of zinc chloride, in a concentration of about 3% by weight in glycerol.

Other zinc salts that could be used to replace all or part of the zinc chloride are the citrate, acetate, lactate, salicylate, and, in general, glycerol soluble, pharmaceutically acceptable zinc salts.

While it is presently preferred to have glycerol as the sole vehicle, it may be diluted with water or another orally acceptable vehicle compatible therewith, such as ethanol, propylene glycol or sorbitol, so long as the glycerol concentration is at least about 25% by weight, preferably in excess of 50% by weight.

The zinc salt concentration (based on the entire composition) will generally vary between about 0.5 and about 8%, preferably between about 1 and about 5% by weight. While higher concentrations could be used, no particular advantage would be afforded thereby, and there are some contraindications in the literature, as noted above.

The compositions of the invention may be in the form of a mouthwash, toothpaste, gel, solution or other form suitable for oral application. Any pharmaceutically acceptable materials such as those ordinarily used in such oral compositions that are compatible with the zinc chloride or other salt as well as with the glycerol vehicle may be employed in the compositions of this invention.

In accordance with the present invention, the compositions are applied to the gingiva manually, preferably with gentle rubbing of the gingiva. In accordance with a preferred method of treatment, the user first brushes his teeth with a conventional dentifrice and then applies the composition of the present invention to the gums by gently rubbing with the forefinger on both the buccal and lingual sides, preferably at least once daily, more preferably twice daily.

The following examples will further serve to illustrate the composition of this invention.

EXAMPLE I

Anti-gingivitis solution

| | |
|---|---|
| Zinc chloride | 2.7% w/w |
| Glycerol, U.S.P. | 96.3% |
| Flavors | 1.0% |

EXAMPLE II

Mouthwash

| | |
|---|---|
| Zinc chloride | 1.0% w/w |
| Glycerol | 25.0% |
| Ethyl alcohol, U.S.P. | 15.0% |
| Sorbitol | 5.0% |
| Flavor | 1.0% |
| Deionized water | 53.0% |
| | 100.0% |

EXAMPLE III

Toothpaste

| | |
|---|---|
| Zinc chloride | 4.0% w/w |
| Glycerol | 25.0% |
| Dicalcium phosphate dihydrate | 40.0% |
| Sodium carboxymethyl-cellulose (CMC) | 1.0% |
| Sorbitol | 10.0% |
| Flavors | 1.0% |

-continued

| | |
|---|---|
| Propylene glycol | 5.0% |
| Deionized water | 13.3% |
| Preservative | 0.1% |
| Carboxyvinyl polymer (Carbopol 934) | 0.5% |
| Sodium hydroxide, 50% soln. | 0.1% |
| | 100.0% |

EXAMPLE IV

Toothpaste

| | |
|---|---|
| Glycerol | 45.0% w/w |
| CMC | 0.8% |
| Dical phosphate | 40.0% |
| Calcium carbonate | 5.0% |
| Flavor | 1.0% |
| Preservative | 0.7% |
| Zinc chloride | 4.0% |
| Deionized water | 3.5% |
| | 100.0% |

EXAMPLE V

Toothgel

| | |
|---|---|
| Glycerol | 90.0% w/w |
| CMC | 0.8% |
| Carbopol 934 | 2.0% |
| Deionized water | 4.3% |
| Zinc chloride | 1.0% |
| Sodium hydroxide, 50% soln. | 0.2% |
| Flavor | 1.0% |
| Preservative | 0.7% |
| | 100.0% |

Variations can, of course, be made without departing from the spirit and scope of the invention.

What is claimed is:

1. A method for treating gingivitis which comprises topically applying to the gums of a patient in need of such treatment an effective amount for treating gingivitis of a composition which consists essentially of at least about 50% by weight of glycerol and from about 0.5 to 8% by weight of a pharmaceutically acceptable zinc salt that is soluble in said glycerol.

2. The method of claim 1 wherein said zinc salt is selected from the group consisting of the chloride, citrate, acetate, lactate and salicylate.

3. The method of claim 2 wherein said salt is zinc chloride.

4. The method of claim 1 wherein said zinc salt concentration is from about 1 to about 5% by weight.

5. The method of claim 4 wherein said zinc salt concentration is about 3% by weight.

6. The method of claim 1 wherein said composition consists essentially of glycerol and from about 1 to about 5% by weight zinc chloride.

7. The method of claim 6 wherein said composition contains about 3% by weight zinc chloride.

8. The method of claim 1 wherein said application is performed daily.

9. The method of claim 1 which comprises rubbing the gums with the composition.

10. The method of claim 8 which includes brushing of the teeth with a conventional dentifrice before said application of said composition.

* * * * *